(12) United States Patent
Fazi et al.

(10) Patent No.: US 9,757,306 B2
(45) Date of Patent: Sep. 12, 2017

(54) VIAL CONTAINER WITH COLLAR CAP

(71) Applicant: BAYER MEDICAL CARE INC., Indianola, PA (US)

(72) Inventors: Bruno Fazi, Pittsburgh, PA (US); Jason L. Bazala, Irwin, PA (US); Arthur E. Uber, III, Pittsburgh, PA (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 0 days.

(21) Appl. No.: 14/775,988

(22) PCT Filed: Mar. 10, 2014

(86) PCT No.: PCT/US2014/022448
§ 371 (c)(1),
(2) Date: Sep. 14, 2015

(87) PCT Pub. No.: WO2014/164444
PCT Pub. Date: Oct. 9, 2014

(65) Prior Publication Data
US 2016/0030286 A1    Feb. 4, 2016

(51) Int. Cl.
*G21F 5/12* (2006.01)
*F16L 39/00* (2006.01)
(Continued)

(52) U.S. Cl.
CPC ............ *A61J 1/16* (2013.01); *B65D 51/00* (2013.01); *B65D 53/02* (2013.01);
(Continued)

(58) Field of Classification Search
USPC .................. 220/23.87, 230, 324, 23.86, 315; 206/1.5, 818, 438; 215/221; 250/507.1,
(Continued)

(56) References Cited

U.S. PATENT DOCUMENTS

| | | |
|---|---|---|
| 1,427,820 A | 9/1922 | Kaufman |
| 1,609,447 A | 12/1926 | Ward |

(Continued)

FOREIGN PATENT DOCUMENTS

| | | |
|---|---|---|
| DE | 102007029587 A1 | 1/2009 |
| EP | 0915760 B1 | 5/2002 |

(Continued)

OTHER PUBLICATIONS

The Supplementary European Search Report from EP Application No. EP13799972 dated Dec. 21, 2015.
(Continued)

*Primary Examiner* — J. Gregory Pickett
*Assistant Examiner* — Gideon Weinerth
(74) *Attorney, Agent, or Firm* — Joseph L. Kent; David Schramm; James R. Stevenson (57) ABSTRACT

Vial containers including a collar which is attached to a vial or incorporated into a vial cap, a cap designed to receive a portion of the collar while covering the vial, and a container designed to receive a portion of the collar and encase the body of the vial are described herein. The collar, generally, includes a means for reversibly attaching to the cap and container.

17 Claims, 6 Drawing Sheets

(51) Int. Cl.
*A61J 1/16* (2006.01)
*B65D 77/04* (2006.01)
*B65D 51/00* (2006.01)
*B65D 53/02* (2006.01)
*G21F 5/015* (2006.01)
*A61M 5/178* (2006.01)

(52) U.S. Cl.
CPC ......... *B65D 77/0486* (2013.01); *G21F 5/015* (2013.01); *A61M 5/1785* (2013.01); *B65D 2313/04* (2013.01)

(58) Field of Classification Search
USPC ............ 250/428, 506.1, 370.01, 252.1, 394, 250/505.1; 141/311 R; 976/DIG. 351, 976/DIG. 352, DIG. 354; 600/5, 7; 411/970, 560; 267/167; 285/318, 321; 403/326, 357
See application file for complete search history.

(56) References Cited

U.S. PATENT DOCUMENTS

| | | | |
|---|---|---|---|
| 1,780,728 A | 11/1930 | Webber | |
| 1,875,325 A | 9/1932 | Bowman et al. | |
| 1,918,307 A | 7/1933 | Webber | |
| 1,918,308 A | 7/1933 | Webber | |
| 2,364,126 A * | 12/1944 | Cantor | B65D 51/002 215/247 |
| 2,487,728 A | 11/1949 | Quiring | |
| 2,492,326 A | 12/1949 | Scotti | |
| 2,682,352 A | 6/1954 | Hawkins et al. | |
| 2,761,717 A | 9/1956 | Mahlke | |
| 2,915,640 A | 12/1959 | Grubel et al. | |
| 3,027,034 A | 3/1962 | Christian | |
| 3,256,441 A * | 6/1966 | Grasty | G21F 5/015 206/204 |
| 3,308,980 A | 3/1967 | Taylor | |
| 3,369,121 A | 2/1968 | Bruno et al. | |
| 3,432,666 A | 3/1969 | Geoffrey et al. | |
| 3,465,905 A * | 9/1969 | Schottanes | A47J 41/02 206/543 |
| 3,531,644 A | 9/1970 | Curtis | |
| 3,630,403 A | 12/1971 | Robert | |
| 3,655,985 A | 4/1972 | James et al. | |
| 3,673,411 A | 6/1972 | Herman | |
| 3,718,138 A | 2/1973 | Alexandrov et al. | |
| 3,754,141 A | 8/1973 | Leebl et al. | |
| 3,811,591 A | 5/1974 | Novitch | |
| 3,850,325 A | 11/1974 | MacLeod | |
| 3,882,315 A | 5/1975 | Soldan | |
| 3,896,958 A | 7/1975 | Robbins et al. | |
| 3,968,871 A * | 7/1976 | Briscoe | B65D 50/04 206/1.5 |
| 3,971,955 A | 7/1976 | Heyer et al. | |
| 3,973,554 A | 8/1976 | Tipton | |
| 3,984,695 A | 10/1976 | Collica et al. | |
| 3,993,063 A | 11/1976 | Larrabee | |
| 4,020,355 A | 4/1977 | Czaplinski et al. | |
| 4,060,073 A * | 11/1977 | Collica | G21F 5/018 250/506.1 |
| 4,074,824 A | 2/1978 | Kontes | |
| 4,081,688 A | 3/1978 | Fries | |
| 4,084,097 A | 4/1978 | Czaplinski et al. | |
| 4,092,546 A | 5/1978 | Larrabee | |
| 4,122,836 A | 10/1978 | Burnett | |
| 4,144,461 A | 3/1979 | Glasser et al. | |
| 4,307,713 A | 12/1981 | Galkin et al. | |
| 4,382,512 A | 5/1983 | Furminger | |
| 4,401,108 A | 8/1983 | Galkin et al. | |
| 4,409,966 A | 10/1983 | Lambrecht et al. | |
| 4,562,829 A | 1/1986 | Bergner | |
| 4,567,014 A | 1/1986 | Popp et al. | |
| 4,585,009 A | 4/1986 | Barker et al. | |
| 4,594,214 A | 6/1986 | Popp et al. | |
| 4,673,813 A | 6/1987 | Sanchez | |
| 4,738,388 A | 4/1988 | Bienek et al. | |
| 4,811,858 A | 3/1989 | Augur | |
| 4,846,235 A * | 7/1989 | Handke | G21F 5/018 141/27 |
| 4,865,189 A | 9/1989 | Guerra et al. | |
| 4,923,088 A * | 5/1990 | Tanaka | B65D 41/3404 215/12.1 |
| 4,982,769 A | 1/1991 | Fournier et al. | |
| 5,027,966 A | 7/1991 | Yadock | |
| 5,042,679 A | 8/1991 | Crowson et al. | |
| 5,160,021 A * | 11/1992 | Sibley | B01L 9/06 206/204 |
| 5,274,239 A | 12/1993 | Lane et al. | |
| 5,303,836 A | 4/1994 | Childress | |
| 5,316,146 A | 5/1994 | Graff | |
| 5,437,387 A | 8/1995 | Burns | |
| 5,442,186 A | 8/1995 | Walker et al. | |
| 5,472,403 A | 12/1995 | Cornacchia et al. | |
| 5,514,071 A | 5/1996 | Sielaff, Jr. et al. | |
| 5,519,931 A | 5/1996 | Reich | |
| 5,624,410 A | 4/1997 | Tsukada | |
| 5,695,090 A | 12/1997 | Burdick | |
| 5,725,114 A | 3/1998 | Pickman | |
| 5,817,067 A | 10/1998 | Tsukada | |
| 5,828,073 A | 10/1998 | Zhu et al. | |
| 5,834,788 A | 11/1998 | Fu et al. | |
| 5,857,579 A | 1/1999 | Finneran | |
| 5,865,805 A | 2/1999 | Ziemba | |
| 5,904,267 A | 5/1999 | Thompson | |
| 5,927,351 A | 7/1999 | Zhu et al. | |
| 5,944,190 A | 8/1999 | Edelen | |
| 5,993,425 A | 11/1999 | Kriesel | |
| 6,159,144 A * | 12/2000 | Angel | A61M 5/1785 600/5 |
| 6,162,198 A | 12/2000 | Coffey et al. | |
| 6,323,501 B1 * | 11/2001 | White | G21F 5/015 250/423 R |
| 6,425,174 B1 | 7/2002 | Reich | |
| 6,585,684 B1 | 7/2003 | Hughett et al. | |
| 6,586,758 B2 | 7/2003 | Martin | |
| 6,589,158 B2 | 7/2003 | Winkler | |
| 6,614,040 B1 | 9/2003 | Zens | |
| 6,717,163 B2 * | 4/2004 | Zens | G21F 5/018 128/846 |
| 6,767,319 B2 | 7/2004 | Reilly et al. | |
| 6,773,673 B1 | 8/2004 | Layfield et al. | |
| 6,989,543 B2 * | 1/2006 | Drobnik | G21G 4/00 250/453.11 |
| 7,040,856 B2 | 5/2006 | Reich | |
| 7,086,133 B2 | 8/2006 | Reich | |
| 7,105,846 B2 | 9/2006 | Eguchi | |
| 7,151,267 B2 | 12/2006 | Lemer | |
| 7,170,072 B2 | 1/2007 | Schwarz et al. | |
| 7,199,375 B2 | 4/2007 | Drobnik et al. | |
| 7,307,265 B2 | 12/2007 | Polsinelli et al. | |
| 7,419,478 B1 | 9/2008 | Reilly et al. | |
| 7,425,195 B2 | 9/2008 | Wissman et al. | |
| 7,546,855 B2 | 6/2009 | Rodewald | |
| 7,694,610 B2 | 4/2010 | Flores et al. | |
| 7,753,835 B2 | 7/2010 | Van Der Lee et al. | |
| 7,772,565 B2 | 8/2010 | Wilson | |
| 7,812,322 B2 | 10/2010 | Wagner et al. | |
| 7,842,023 B2 | 11/2010 | Chinol et al. | |
| 7,934,614 B2 | 5/2011 | Finneran | |
| 7,975,733 B2 | 7/2011 | Horppu et al. | |
| 8,003,967 B2 * | 8/2011 | Fago | G21F 5/015 250/432 R |
| 8,044,377 B2 | 10/2011 | Helle et al. | |
| 8,251,221 B1 | 8/2012 | Castaneda | |
| 8,409,165 B2 | 4/2013 | Niedospial, Jr. et al. | |
| 8,496,272 B2 | 7/2013 | Davis | |
| 8,505,787 B2 | 8/2013 | Fox et al. | |
| 8,633,461 B2 | 1/2014 | Fago et al. | |
| 8,678,229 B1 * | 3/2014 | Alford | A61J 1/16 220/592.2 |

(56) References Cited

U.S. PATENT DOCUMENTS

| | | | |
|---|---|---|---|
| 9,004,281 B1* | 4/2015 | Castaneda | B65D 81/02 206/446 |
| 9,267,526 B2* | 2/2016 | Balsells | F16B 21/18 |
| 9,312,630 B2* | 4/2016 | Huang | |
| 9,324,466 B2* | 4/2016 | Helle | G21F 5/015 |
| 9,327,886 B2* | 5/2016 | Fazi | G21F 5/015 |
| 2003/0094812 A1* | 5/2003 | Balsells | F16L 37/084 285/318 |
| 2003/0222228 A1 | 12/2003 | Chen et al. | |
| 2003/0226981 A1 | 12/2003 | Schmidt | |
| 2004/0015038 A1 | 1/2004 | Lemer | |
| 2004/0084340 A1 | 5/2004 | Morelle et al. | |
| 2004/0254525 A1 | 12/2004 | Uber et al. | |
| 2005/0085682 A1 | 4/2005 | Sasaki et al. | |
| 2005/0107698 A1 | 5/2005 | Powers et al. | |
| 2005/0154275 A1 | 7/2005 | Chinol et al. | |
| 2005/0203329 A1 | 9/2005 | Muto et al. | |
| 2005/0203330 A1 | 9/2005 | Muto et al. | |
| 2005/0224728 A1 | 10/2005 | Schwarz et al. | |
| 2005/0234424 A1 | 10/2005 | Besing et al. | |
| 2005/0247893 A1 | 11/2005 | Fu et al. | |
| 2005/0277833 A1 | 12/2005 | Williams, Jr. | |
| 2006/0076520 A1* | 4/2006 | Drobnik | A61L 2/07 250/506.1 |
| 2006/0086909 A1 | 4/2006 | Schaber | |
| 2006/0151048 A1 | 7/2006 | Tochon-Danguy et al. | |
| 2006/0293553 A1 | 12/2006 | Polsinelli et al. | |
| 2007/0034537 A1 | 2/2007 | Fago et al. | |
| 2007/0108205 A1* | 5/2007 | Porras | A61J 1/1412 220/23.87 |
| 2007/0129591 A1 | 6/2007 | Yanke et al. | |
| 2008/0177126 A1 | 7/2008 | Tate et al. | |
| 2008/0197302 A1 | 8/2008 | Fago et al. | |
| 2008/0200747 A1 | 8/2008 | Wagner et al. | |
| 2008/0242915 A1 | 10/2008 | Jackson et al. | |
| 2008/0265183 A1* | 10/2008 | Sirach | G21F 5/015 250/506.1 |
| 2009/0069625 A1 | 3/2009 | Helle et al. | |
| 2010/0019174 A1 | 1/2010 | Helle et al. | |
| 2010/0032591 A1 | 2/2010 | Lemer | |
| 2010/0049159 A1 | 2/2010 | Fangrow | |
| 2010/0160889 A1 | 6/2010 | Smith et al. | |
| 2010/0168712 A1 | 7/2010 | Tuckwell et al. | |
| 2010/0185040 A1 | 7/2010 | Uber, III et al. | |
| 2011/0124948 A1 | 5/2011 | Yokell | |
| 2011/0132907 A1 | 6/2011 | Hajichristou et al. | |
| 2011/0178359 A1 | 7/2011 | Hirschman et al. | |
| 2011/0201867 A1 | 8/2011 | Wagner | |
| 2011/0209764 A1 | 9/2011 | Uber et al. | |
| 2011/0214781 A1 | 9/2011 | Horppu et al. | |
| 2011/0215267 A1 | 9/2011 | Fago et al. | |
| 2012/0007004 A1 | 1/2012 | Valentin et al. | |
| 2012/0305800 A1 | 12/2012 | Mayfield et al. | |
| 2013/0001446 A1 | 1/2013 | Sakashita | |
| 2013/0149029 A1* | 6/2013 | Changsrivong | F16B 17/00 403/361 |
| 2014/0046295 A1 | 2/2014 | Uber, III et al. | |
| 2014/0048432 A1 | 2/2014 | Kakiuchi et al. | |
| 2014/0179148 A1* | 6/2014 | Huang | F16B 21/186 439/359 |
| 2014/0259617 A1* | 9/2014 | Kompa | F16F 1/045 29/450 |
| 2015/0123021 A1 | 5/2015 | Isensee | |
| 2015/0325321 A1 | 11/2015 | Helle et al. | |
| 2016/0030286 A1* | 2/2016 | Fazi | A61J 1/16 220/230 |

FOREIGN PATENT DOCUMENTS

| | | |
|---|---|---|
| EP | 1616587 A1 | 1/2006 |
| EP | 1927996 A2 | 6/2008 |
| JP | 2004290455 A | 10/2004 |
| JP | 2005283431 A | 10/2005 |
| WO | 2004004787 A2 | 1/2004 |
| WO | 2006051531 A2 | 5/2006 |
| WO | 2006124775 A2 | 11/2006 |
| WO | 2007010534 A2 | 1/2007 |
| WO | 2007056654 A1 | 5/2007 |
| WO | 2008083313 A2 | 7/2008 |
| WO | 2009/107930 | 9/2009 |
| WO | 2009/142944 | 11/2009 |
| WO | 2009149367 A1 | 12/2009 |
| WO | 2012019201 A2 | 2/2012 |

OTHER PUBLICATIONS

International Preliminary Report on Patentability for Application No. PCT/US2013/044031, dated Dec. 9, 2014, 7 pages.

International Preliminary Report on Patentability for Application No. PCT/US2013/048484, dated Dec. 31, 2014, 6 pages.

International Search Report and Written Opinion for Application No. PCT/US2013/044031, dated May 28, 2014, 8 pages.

International Search Report and Written Opinion for Application No. PCT/US2013/048484, dated Oct. 22, 2013, 8 pages.

International Search Report and Written Opinion for Application No. PCT/US2014/022448, dated Jul. 15, 2014, 8 pages.

The International Preliminary Report on Patentability dated Sep. 24, 2015 from corresponding PCT Application No. PCT/US2014/022448.

"Supplementary European Search Report from EP Application No. EP14779338", dated Oct. 13, 2016.

* cited by examiner

VIAL CONTAINER WITH COLLAR CAP

CROSS REFERENCE TO RELATED APPLICATIONS

This application claims the benefit of U.S. application Ser. No. 13/802,669, now U.S. Pat. No. 9,327,886, filed Mar. 13, 2013 and entitled "Vial Container with Collar Cap," and which is incorporated herein in its entirety.

This application is a U.S. National Phase entry under 35 U.S.C §371 of International Application No. PCT/US2014/022448, filed Mar. 10, 2014, which claims the benefit of U.S. application Ser. No. 13/802,669, filed Mar. 13, 2013 and entitled "Vial Container with Collar Cap," and which is incorporated herein in its entirety

BACKGROUND

Administration of radioactive pharmaceutical substances or drugs, generally termed radiopharmaceuticals, is often used in the medical field to provide information or imagery of internal body structures and/or functions including, but not limited to, bone, vasculature, organs and organ systems, and other tissue or as therapeutic agents to kill or inhibit the growth of targeted cells or tissue, such as cancer cells. Radiopharmaceutical agents used in imaging procedures and therapeutic procedures typically include highly radioactive nuclides of short half-lives and are hazardous to attending medical personnel. These agents are toxic and can have physical and/or chemical effects for attending medical personnel such as clinicians, imaging technicians, nurses, and pharmacists. Excessive radiation exposure is harmful to attending medical personnel due to their occupational repeated exposure to the radiopharmaceuticals. The constant and repeated exposure of medical personnel and patients to radiopharmaceuticals over an extended period of time is a significant problem in the nuclear medicine field.

SUMMARY OF THE INVENTION

Embodiments described herein are directed to receptacles for vials holding harmful fluids that include a cap, a container, and a collar having a means for attaching to both the cap and the container. In various embodiments, the collar may attach to a cap on the vial, and in some embodiments, the collar may include a septum and may be used in place of the standard vial cap.

Various embodiments include a vial container including a collar, a cap, and a container. In some embodiments, the container may be configured to receive a portion of the collar and to fixedly or removably attach to a portion of the collar, and in some embodiments, the cap may be configured to receive a portion of the collar and to removeably attach to the collar. In certain embodiments, the collar may include a first attachment means for facilitating an attachment with the container, and in some embodiments, the first attachment means may include, for example, a flex-ring, threads, a crimped portion, attachment pins, and the like and combinations thereof. In particular embodiments, the collar may include a second attachment means for facilitating an attachment with the cap, and in some embodiments, the second attachment means may be, for example, a flex-ring, threads, a crimped portion, attachment pins, and the like and combinations thereof. The collar, the container, or combinations thereof of various embodiments may further include a means for attaching to a device, and in some embodiments, the collar, the container, or combinations thereof may include a flex-ring, threads, attachment pins, and combinations thereof.

In certain embodiments, the collar may include one or more of a lower groove and upper groove or combinations thereof, and in some embodiments, the collar may include a magnetic material disposed in a lower groove, an upper groove, or a combination thereof. According to various embodiments, the lower and/or upper groove may be a continuous or discontinuous groove. In various embodiments, the collar may include a vial groove on an inner surface of the collar, and in some embodiments, a spring may be disposed in the vial groove. The collar may include a upper flange providing an upper opening on the collar, and in particular embodiments, the collar may include a lower flange.

In certain embodiments, the container may include an inner groove, such as a continuous or discontinuous groove. In some embodiments, a flex ring disposed in the inner groove, and in other embodiments, the inner groove may include a magnetic material.

The cap of various embodiments may include a cylindrical lower portion having an interior groove, such as a continuous or discontinuous groove. In some embodiments, the cap may include a flex-ring or magnetic material disposed in the interior groove.

Other embodiments are directed to a vial container including a collar comprising a first attachment means for facilitating an attachment with a container and a second attachment means for facilitating an attachment with the cap, a cap configured to receive a portion of the collar, and a container configured to receive a portion of the collar. Additional embodiments include a vial container including a collar, a cap configured to receive a portion of the collar, and a container configured to receive a portion of the collar.

BRIEF DESCRIPTION OF THE DRAWINGS

In the following detailed description, reference is made to the accompanying drawings, which form a part hereof. In the drawings, similar symbols typically identify similar components unless context dictates otherwise. The illustrative embodiments described in the detailed description, drawings, and claims are not meant to be limiting. Other embodiments may be utilized and other changes may be made, without departing from the spirit or scope of the subject matter presented herein. It will be readily understood that the aspects of the present disclosure, as generally described herein and illustrated in the figures, can be arranged, substituted, combined, separated, and designed in a wide variety of different configurations, all of which are explicitly contemplated herein.

DETAILED DESCRIPTION

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this document is to be construed as an admission that the embodiments described in this document are not entitled to antedate such disclosure by virtue of prior invention.

This disclosure is not limited to the particular systems, devices and methods described, as these may vary. The terminology used in the description is for the purpose of describing the particular versions or embodiments only, and is not intended to limit the scope.

The word "proximal" refers to a direction relatively closer to a clinician using the device described herein, and the word "distal" refers to a direction relatively further from the clinician. For example, the end of a catheter placed within the body of a patient is considered a distal end of the catheter, while the catheter end remaining outside the body is a proximal end of the catheter.

Embodiments of the invention are generally directed to enclosures and enclosure systems for vials including a cap, a container, and a vial collar that is capable of reversibly attaching to both the cap and the container, and methods for using such enclosures for storage of hazardous materials such as, for example, radioactive substances and radiopharmaceuticals. Other embodiments are directed to utensils and tools configured to connect to various parts of enclosure and, in certain embodiments, utensils and tools for connecting to the collar, that allow a user to transport and manipulate the vial without physically contacting the vial or the contents of the vial. The devices and systems of such embodiments may allow for safe storage and transfer of hazardous materials with reduced likelihood of user contact with the hazardous materials during transfer.

Figure 1:
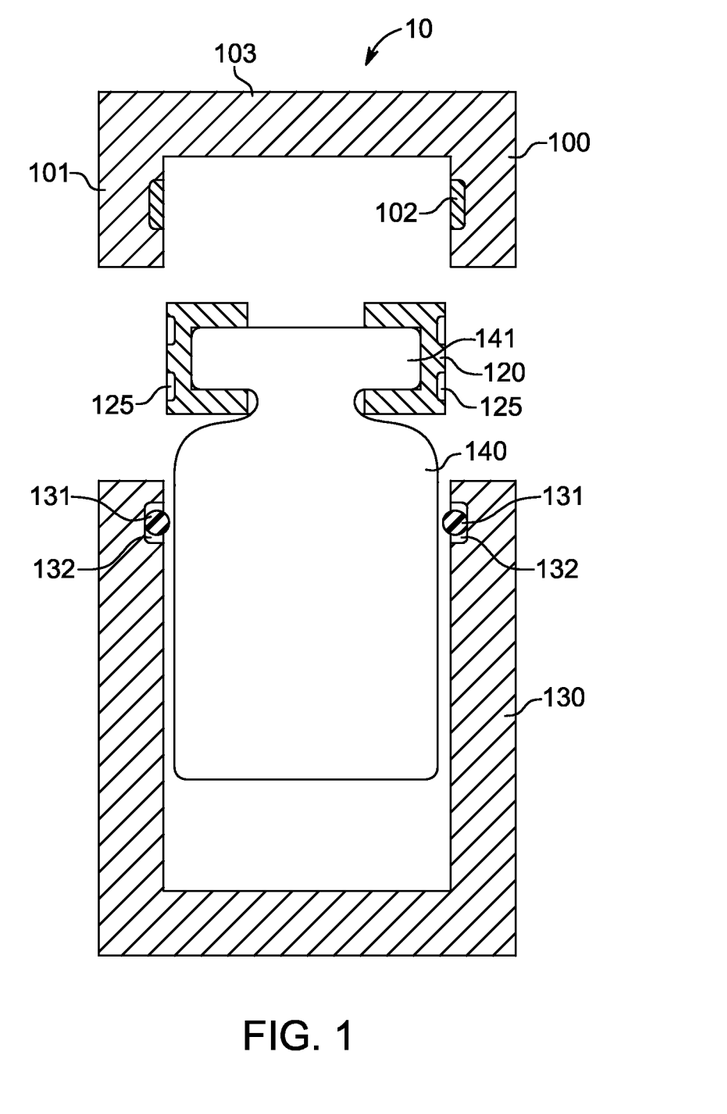
FIG. 1 is a drawing showing a vial container system including a collar, container, and cap.

As illustrated in FIG. 1 in some embodiments, the enclosure 10 may include a cap 100, a collar 120, and a container 130. The collar 120 of such embodiments may have a generally cylindrical shape with an internal circumferential bore 120 sized to receive a flange or lip 141 portion of the vial 140. The collar 120 may be removably received by at least a first portion of the container 130, and in some embodiments, the collar 120 may be reversibly connected to the container 130 by some connection means. Similarly, the collar 120 may be removably received by at least a portion of the cap 100, and in some embodiments, the collar 120 may be reversibly connected to the cap 100 by some connection means. In such embodiments, the vial 140 may be completely encased by the container and the cap, and in certain embodiments, the vial 140 may be spaced from the container 130 and the cap 100 when encased such that the collar 120 may be the only component of the system in physical contact with the vial 140.

The collar 120 may typically have a generally cylindrical shape with an outer surface configured to contact the container 130 and cap 100 and an inner surface configured to attach to the vial 140. In some embodiments, the collar 120 may be composed of a material that is capable of forming a connection with the cap 100 and the container 130. For example, the collar 120 may be composed in whole or in part of steel and magnets may be embedded in the cap 100 and container 130 to facilitate a connection between the collar 120 and the cap 100, container 130 or combinations thereof. In other embodiments, the collar 120 may be composed on a non-magnetic material but one or more magnets that are capable of connecting with the cap 100, container 130, or combination thereof may be embedded in the collar 120.

In still other embodiments, a physical connection may be made between the collar 120 and the cap 100, container 130, or combinations thereof. For example, in some embodiments that collar 120 may include a circumferential groove 132 configured and arranged to accept a ring 131, such as a flexring, confined in a circumferential, continuous groove 132 in an inner surface of the container 130. In operation, the ring 131 will become enclosed by the circumferential groove 125 of the collar 120 and the circumferential groove 132 of the container 130 when the circumferential groove 125 of the collar 120 and the circumferential groove 132 of the container 130 meet connecting the collar 120 to the container 130 and holding the collar 120 and, by extension the vial 140 in place in the container 130. In other embodiments, the ring may be confined in the circumferential groove 125 of the collar 120 rather than the container 130. While this example describes using a ring connector to connect the collar 120 to the container 130, similar components may be used to connect the collar 120 to the cap 100. In particular embodiments, separate ring type connectors can be used to connect the collar 120 to both the container 130 and the cap 100.

In particular embodiments, a combination of means for connecting the collar 120 to the cap 100 and container 130 may be used to reversibly connect the various components of the system. For example, in certain embodiments, the collar 120 may be composed of a magnetic material such as steel that allows for a connection to be made with magnets 102 embedded in the cap 100 and a circumferential groove 125 may be provided to connect to a ring type connector 131 enclosed in a circumferential continuous or discontinuous groove 132 in the container 130. Thus, the collar 120 and vial 140 may be held in the container 130 by a physical connection, and the cap 100 may be held in contact with the collar 120 by a magnetic connection. In use, the magnetic connection between the cap 100 and collar 120 may be easier to break than the physical connection between the collar 120 and the container 130. The user may, therefore, be able to remove the cap 100 without removing vial 140 which remains encased in the container 130 by virtue of the physical connection of the collar 120 with the container 130. Other means for providing a dual connector cap can be used to connect the collar 120 to the cap 100 and container 130 that allow for preferential removal of the cap 100 and can be used in other embodiments.

Figure 2:
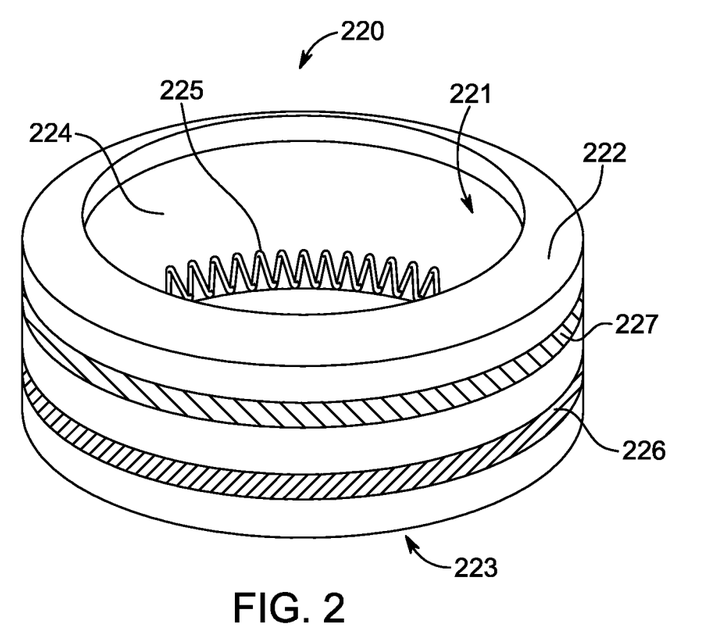
FIG. 2 is a drawing showing the features of an example of a collar.

A more detailed illustration of a collar according to certain embodiments is provided in FIG. 2. As illustrated, in some embodiments, the collar 220 may include an upper flange 222 and a lower flange 223 that provide a vial groove 221 on at least a portion of an inner surface of the collar 220. The dimensions of the collar 220 may vary among embodiments depending of the size and shape of the vial and vial cap that the collar is designed to encapsulate. In particular, the height of the collar 220 (i.e., the distance between the upper flange 222 and the lower flange 223) may be slightly larger than the height of the vial cap that the collar 220 is designed to encapsulate such that the vial cap fits snuggly within the vial groove 221 such that upper flange 222, lower flange 223, and inner surface 224 of the collar 220 contact at least a portion of the vial cap. In other embodiments, the collar 220 may be larger than the vial cap to which it is designed to connect allowing a gap to be created when the collar 220 is attached to the vial cap.

In various embodiments, a spring 225, rubber ring, or other means for holding the vial cap in place may be disposed in the gap. Thus for the collar 220 depicted in FIG. 2, at least a portion of the vial cap may contact the upper flange 222 and the inner surface 224 of the collar 220 directly and the spring 225 may contact the lower flange 223 and the vial cap holding the vial cap and the vial in place by pushing the vial cap toward the upper flange 222. The spring 225 or other means disposed in the gap may further provide a means for introducing the vial cap into the collar 220. For example, the spring 225 may allow the circumference of the opening created by the lower flange 223 to expand as the vial cap is pressed against the spring 225. Once the vial cap has been received in the vial groove 221, the spring 225 may constrict around the neck of the vial preventing movement of the vial cap out of the vial groove by pushing a lower lip of the vial cap toward the upper flange 222.

The upper flange 222 and lower flange 223 of various embodiments may have a width that is the same or different and that may vary based, for example, on the size of the vial, the size of the lip or flange portion of the vial, and combinations thereof. For example, in some embodiments, the upper flange 222 and the lower flange 223 may have substantially equal widths. In other embodiments, the upper flange 222 may have a larger width than the lower flange 223, and the width of the lower flange 223 may be limited by the size of the vial.

The collar 220 may substantially cover the outer circumference of the cap of the vial. In certain embodiments, the upper flange 222 of the collar 220 may cover at least a portion of the upper (top) surface of the cap of the vial and may provide an opening through which at least a portion of the top surface of the cap can be accessed. For example, a collar 220 configured and arranged to attach to a standard vial for transporting injectable medical fluids and pharmaceuticals having a crimped cap and a septum for providing access to the contents of the vial may include an upper flange 222 that provides an upper opening of sufficient size to provide full or partial access to the septum. According to certain embodiments where a standard collar may be smaller than the vial outer diameter, the collar 220 may be configured so that the outer diameter of collar 220 is greater than or equal to the outer diameter of the vial. The caps for standard vials may have a diameter of from about 25 mm to about 45 mm and the width of the upper flange 222 of such embodiments may be from about 2 mm to about 20 mm such that an opening having a diameter of from about 5 mm to about 30 mm is created depending on the size of the vial and the cap. Standard dimensions and specification for medical injection containers and accessories, such as vials and caps suitable for various embodiments in the present disclosure may be found, for example, in ISO 8362-1 through 8362-7.

As discussed above, the collar 220 may further include various components that allow the collar to reversibly connect to the cap 100 and the container 130 (FIG. 1). In some embodiments, the collar may include one or more circumferential, continuous or discontinuous groove 226 on an outer surface of the collar configured and arranged to accept a ring or other connection means associated with the container 130. For example, in FIG. 2, a circumferential groove 226 is provided near the lower flange 223 of the collar 220 that will be received by the container 130. In some embodiments, more than one circumferential groove similar to the circumferential groove 226 depicted in FIG. 2 may be provided on a lower portion of the outer surface of the collar to allow for a vial to be held at various depths within the container 130. In other embodiments, a circumferential groove may be provided near the upper flange 222 of the collar 220 to facilitate a connection with the cap 100.

In some embodiments, a second means for attachment may be provided on the collar 220. For example, a ring of a magnetic material 227 may be provided on an upper portion of the outer surface of the collar 220 that is positioned to interact with a magnetic material associated with the cap 100 of the enclosure system 10. Magnetic material may include a magnet or a material capable of interacting with the magnet to form a magnetic connection such as steel or other metals. Thus, in some embodiments, the magnetic material 227 may include one or more magnets located about the outer circumference of an upper portion of the outer surface of the collar 220. In other embodiments, the magnetic material 227 may be a metal ring embedded in the collar 220 or enclosed within a circumferential groove in the upper portion of the outer surface of the collar 220. In still other embodiments, the magnetic material 227 may be a combination of metal portions and magnet portions.

In some embodiments, the collar 220 may be designed to fit over the cap of a sealed vial. For example, a collar 220 may be placed on the cap of a sealed vial by pushing the lower flange 223 onto and over the cap of the sealed vial. In such embodiments, the collar 220 may include a means for expanding the opening created by the lower flange 223 when the collar is pressed onto the cap of the vial that constricts around the neck of the vial after the cap has been overcome. In other embodiments, the lower flange 223 may be crimped to attach the collar to the cap of the vial, and in still other embodiments, the collar 220 may include two or more parts that attach around the cap of the vial to facilitate attachment. According to certain embodiments comprising a collar 220 having two or more parts, the collar may be formed from a plastic material or other disposable material. In specific embodiments, the two or more collar parts may be placed around the upper flange or lip 141 of the vial and then help in place, for example, by placing the vial and collar into one of container 130 or cap 100 such that the inner rim of the container or cap hold the two or more parts of collar 220 in place around upper flange or lip 141. According to other embodiments, the two or more collar pieces may be held together by other means, such as one or more hinges, magnets, clips, a clamp, friction, or rubber or spring connectors. For example, the two or more collar pieces may be attached together by one or more hinges that allow collar 220 to encircle upper flange or lip 141. For example, the ends of a hinged collar may be held in place around flange or lip 141 by various retaining means, such as magnets, clips, ties, a clamp, friction (one end slidably inserted between the other end and flange or lip 141), container 130 or cap 100 (see above), or by an elastic (e.g., rubber or other polymer) or spring retaining ring. According to other embodiments, the two or more pieces of the collar may comprise a hinge-less configuration wherein the two or more pieces are held in an encircling conformation around flange or lip 141 by one or more of the retaining means described herein.

In other embodiments, the collar 220 may attach directly to an uncapped vial. For example, in some embodiments, the collar may include a septum covering the opening created by the upper flange 222 and the lower flange 223 may be crimped onto an uncapped vial. In other embodiments, the collar 220 may include an inner surface 224 that includes grooves and ridges for screw type attachment to vial, and in still other embodiments, other attachment means such as, for example, snap on configuration may be used to attach the collar 220 to an uncapped vial. In operation, collars 220 that attach directly to the vial may be placed on the vial during manufacture, or in some embodiments, the vial cap may be removed and replaced with a collar 220 having a septum that is designed to be attached directly to the vial. According to certain embodiments, collar 220 may extend downward around and encase at least a portion of the outer surface of vial 140, for example, to provide stability to the vial and, in embodiments wherein the collar entirely encases vial 140, provide protection from breakage or to contain any leakage of liquid from vial 140.

The collar 220 may be composed on any material known in the art. For example, in various embodiments, the collar 220 may be composed of a polymeric material, metal, composite material, or combinations thereof. In particular embodiments, the collar or portions thereof may be composed of a polymeric material such as a plastic that has been molded to include the various features described above. Various polymers known in the art can be useful in such embodiments, including, but not limited to, acrylic, polycarbonate, polyester, polypropylene, polyacetal, polystyrene, polyamide, polyacrylamide, polyimide, polyolefin, cyclic olefin copolymer, rubber, elastomers, thermosets, thermoplastics, and the like and combinations thereof, and in certain embodiments, low density polyethylene (LDPE), polypropylene (PP), polyacetal (POM), nylon, Santoprene, polyvinyl chloride (PVC), and the like and combinations thereof. In some embodiments, the collar or portions thereof may be composed of a metal or metal alloy such as, but not limited to, aluminum, steel, copper, brass, and the like and combinations thereof.

Figure 3A:
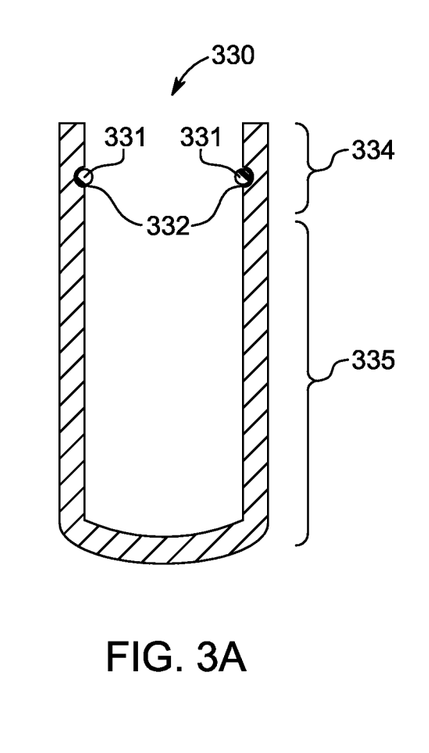
FIG. 3A-C are drawings showing various containers.
Figure 3B:
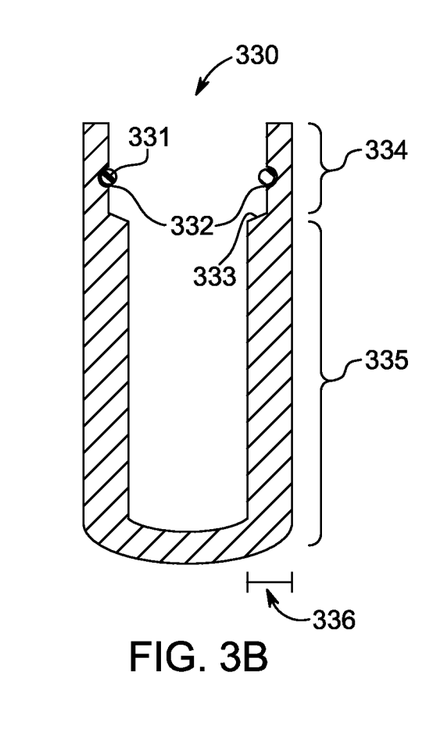
Figure 3C:
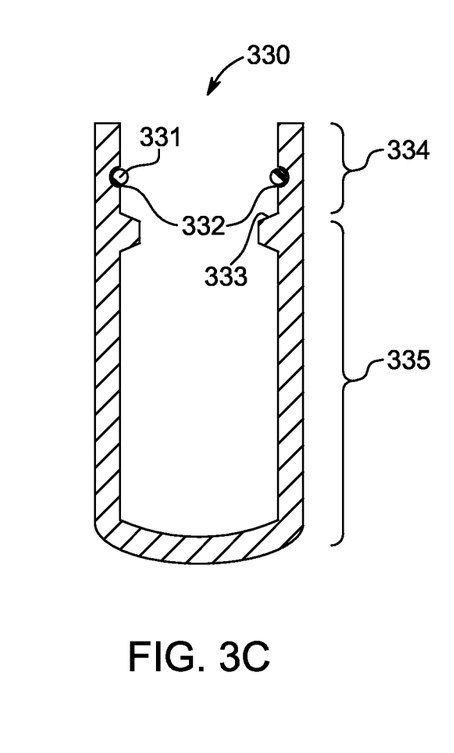

Examples of containers encompassed by various embodiments are provided in FIGS. 3 A-C. In general, the upper portion 334 of the container 330 may be designed to receive at least a portion of the collar, and the container 330 of various embodiments may at least include a means for connecting to the collar 120. For example, a container 330 for connecting to the collar depicted in FIG. 2 may include a circumferential, continuous or discontinuous groove 332 disposed on an inner surface or an upper portion of the container 330. A ring 331 or other means for connecting to the collar 120 may be provided within circumferential groove 332. In other embodiments, a magnetic material may be disposed within the circumferential, continuous or discontinuous groove 332 of the container 330.

To receive the collar 120, the upper portion 334 of the container 330 may have an inner diameter slightly larger than the outer diameter of the collar 120. In some embodiments as depicted in FIG. 3A, the diameter of the upper portion 334 of the container 330 may be substantially the same as the diameter to the lower portions 335 of the container 330. Thus, the container 330 may have a substantially uniform diameter. In other embodiments as depicted in FIG. 3B, the inner diameter of the upper portion 334 of the container 330 may be sized to receive the collar 120 and may be larger than the inner diameter of the lower portion 335 of the container 330 to create a shelf 333 that retains the collar 120 in the upper portion 344 of the container 330. Thus, the shelf 333 may hold the collar in the upper portion 334 of the container to reduce the likelihood of the collar being pushed in to the lower portion 335 of the container. According to another embodiment of container 330 (not shown) having a lower portion 335 with an inner diameter less than that of the upper portion 334 (as shown in FIG. 3B), the outer diameter of lower portion 335 of the container may be reduced so that the thickness 336 of the container wall of lower portion 335 is reduced. According to one embodiment, the wall of lower portion 335 may have a thickness 336 substantially equal to the wall thickness of upper portion 334. In other embodiments, the thickness 336 of the wall of lower portion 335 may be reduced to any thickness, provided that the reduced thickness 336 remains sufficient to block radioactive emissions from the radiopharmaceutical within the vial. Reduction of the thickness 336 of the wall of lower portion 335 in FIG. 3B reduces the amount of excess radiation shielding material, such as tungsten, lead and/or other radiation shielding material described herein, incorporated into lower portion 335. In some embodiments as illustrated in FIG. 3C, a shelf 333 may be disposed between an upper portion 334 and a lower portion 335 having substantially similar diameters. In certain embodiments, the shelf 333 may be an extension of the material making up the walls of the container 330. Thus, the container 330 may be bored from the same material with an upper portion 334 and a lower portion 335 having similar diameters with a ring or material, i.e., the shelf 333, creating a smaller diameter disposed between the upper portion 334 and the lower portion 335. In other embodiments, a shelf 333, as depicted in FIG. 3C, may be composed of a material, that can be the same or different from the material used to make the container, that is inserted into a secondary, continuous or discontinuous groove on the inner surface of the container 330.

The container 330 may be sized to hold a vial and the size of the container may vary depending, for example, on the size of the vial. In some embodiments, the lower portion 335 of the container 330 may be sized to receive a vial of a particular size. For example, a standard vial for holding 2 ml of injectable liquid has a diameter of 12 mm and a height of 32 mm, the lower portion 335 of the container 330 may be sized to receive a vial. In other embodiments, the lower portion 335 of the container 330 may be sized to accommodate various vials having different sizes and shapes. For example, the lower portion 335 of the container 330 may have a diameter and height substantially larger than the diameter and height of the 2 ml vial described above, but the collar may be able to securely hold the vial within the container 330. Therefore, the container may be able to hold substantially larger vials, e.g., 5 ml, 10 ml, 20 ml, etc., as well as the relatively small 2 ml vial described above. According to other embodiments, the container 330 may be configured to hole a standardized collar 120 within upper portion 334 while the lower portion may be configured to hold vials of different lengths, widths and/or geometries. According to these embodiments, the cap 100, collar 120, upper flange or lip 141 and septum of the vial may be substantially uniform and standardized for a variety of vials having differing lengths, widths, and/or geometries, while the container 330 may be configured to contain the vials having differing lengths, widths, and/or geometries, for example by making the inner diameter and/or length of the lower portion 335 generally larger than the maximum length and/or width of the vials to be contained therein. Thus, according to these embodiments, a vial body may be loosely retained and/or restrained within container 330, i.e., at least portions of the outer diameter of the vial may not be in close proximity to the inner wall of the lower portion 335 of container 330. According to various embodiments, the top, i.e., upper flange and lip 141, of the vial may be standardized, for example, according to ISO 8362-1 through 8362-7. According to certain embodiments, the spatial relationship between various portions of the outer diameter of the vial and the inner diameter of the lower portion 335 of container 330 is irrelevant provided that the thickness 336 of the lower portion 335 of the container wall is sufficient to block radioactive emissions from the radiopharmaceutical in the vial.

Figure 5:
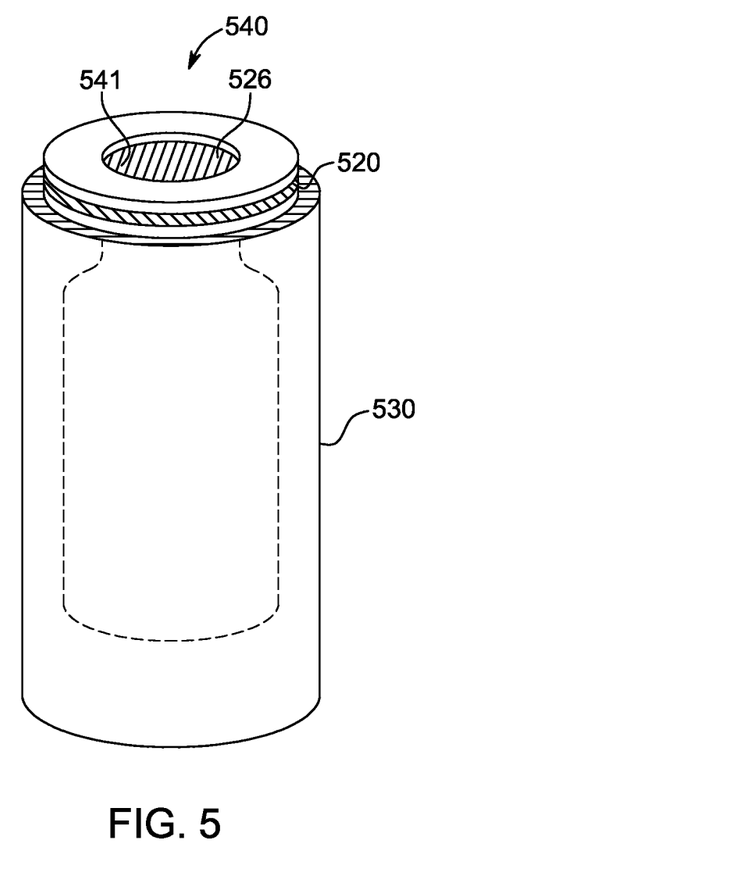
FIG. 5 is a drawing showing a vial attached to a collar and inserted into a container.

FIG. 5 shows a vial 540 that is held in a container 530 by an attachment of the container 530 to the collar 520. The vial 540 includes a septum 541 that can be accessed through an opening 526 in the collar 520. As illustrated, no other part of the vial is accessible to the user, and in embodiments in which the vial holds, for example, radioactive materials, emissions from the radioactive materials may be blocked by the container 530 and collar 520 when the collar 520 and container 530 are composed of a material that is capable of blocking radioactive emissions Such materials include for example, tantalum, tungsten, lead, and combinations thereof, aluminum, aluminum alloy, titanium, titanium alloy, beryllium, beryllium alloy, plastics, and combinations thereof, and various ceramic and polymer matrix materials including such metals.

Figure 6:
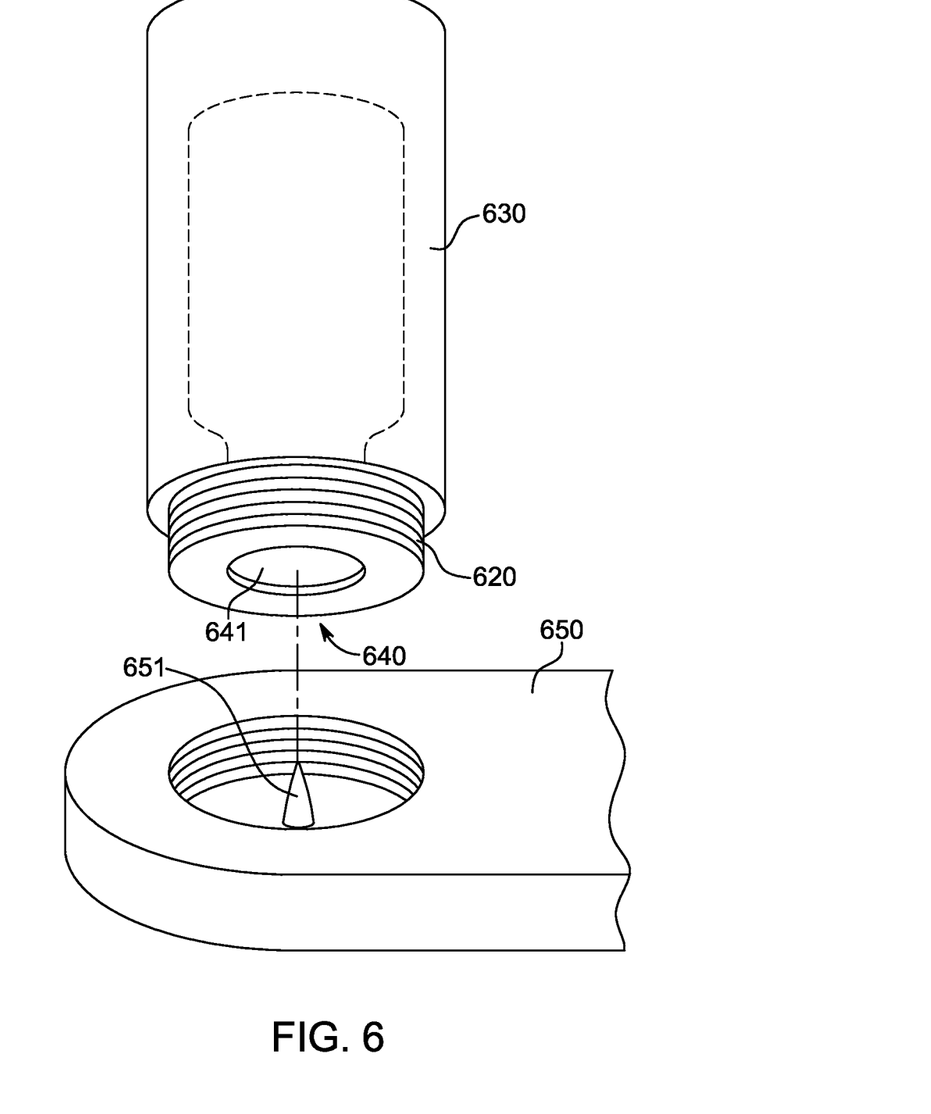
FIG. 6 is a drawings showing a collar and container including an encased vial being attached to a device having a vial spike configured to accept an inverted vial.

In various embodiments, the attachment between the collar 520 and the container 530 may be sufficient to allow the container 530 containing the vial 540 to be inverted. For example, flex-ring containing collar 520 and container 530 combinations described above can provide sufficient stability to allow the container to be inverted while the vial remains attached. In some embodiments, the collar 520 or the container 530 may be configured to allow for the introduction of an inverted container into a larger device. For example as illustrated in FIG. 6, certain devices 650 may include an upright vial spike 651 positioned to accept an inverted vial 640 (not shown held within the container) and pierce septum 641. The collar 620 and the container 630 may include elements that allow the collar 620 or the container 630 to interact with the device 650 to hold the vial in place on the vial spike 651 to allow transfer of fluid from the vial 640 to the device 650, for example through septum 641 via spike 651. For example, FIG. 6 shows a collar 620 and a device having mating grooves and ridges that allow for the collar 620 to be screwed into the device 650. In other embodiments, alignment pins, grooves, ridges, or other means for attachment may be provided on the collar 620 or the container 630 that allow the container 630 and collar 620 housing a vial 640 to dock to the device 650 and the hold the vial in position to allow for removal of the contents of the vial 640.

The container 330, as illustrated in FIG. 3, may be made from any material known in the art, and the choice of material may depend on the hazardous material held within the vial. For example, in various embodiments, the container 330 may be made from a polymeric material, metal, composite material, or combinations thereof. In particular embodiments, the container 330 or portions thereof may be composed of a polymeric material such as a plastic that has been molded to include the various features described above. Various polymers known in the art can be useful in such embodiments, including, but not limited to, acrylic, polycarbonate, polyester, polypropylene, polyacetal, polystyrene, polyamide, polyacrylamide, polyimide, polyolefin, cyclic olefin copolymer, rubber, elastomers, thermosets, thermoplastics, and the like and combinations thereof, and in certain embodiments, low density polyethylene (LDPE), polypropylene (PP), polyacetal (POM), nylon, Santoprene, polyvinyl chloride (PVC), and the like and combinations thereof. In some embodiments, the container 330 or portions thereof may be composed of a metal or metal alloy such as, but not limited to, aluminum, steel, copper, brass, and the like and combinations thereof. In particular embodiments, the container 330 may be designed to hold a radioactive material and may be composed of a material capable of blocking or reducing exposure to high energy radioactive particles. Such materials include for example, tantalum, tungsten, lead, and combinations thereof, aluminum, aluminum alloy, titanium, titanium alloy, beryllium, beryllium alloy, plastics, and combinations thereof, and various ceramic and polymer matrix materials including such metals.

Figure 4A:
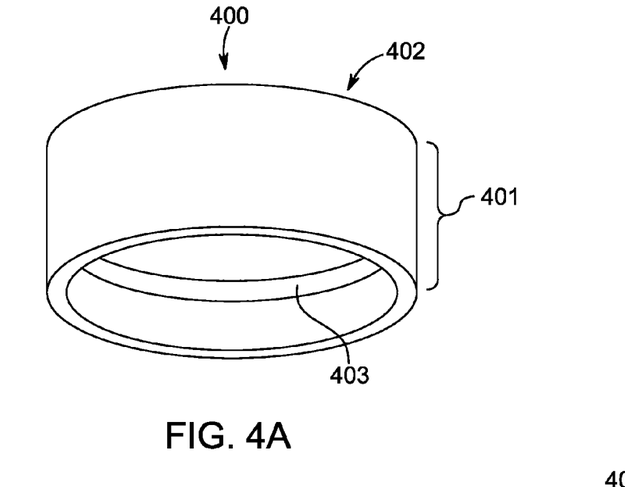
FIG. 4A-C are drawings showing various caps.
Figure 4B:
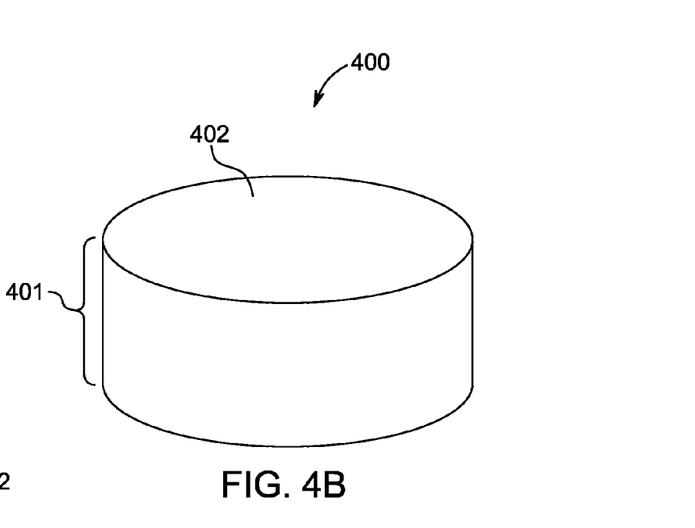

As illustrated in FIG. 1, the cap 100 may be of any size and may be designed to at least contact an upper portion of the collar 120. For example, as illustrated in FIGS. 4A and 4B, the cap 400 may include a cylindrical lower portion 401, and a circular top 402 having a diameter that is about equal to the diameter of the cylindrical lower portion 401 and may cover the upper surface of the cylindrical lower portion 401. In various embodiments, the cylindrical lower portion 401 of the cap 400 may have an outer diameter substantially similar to the outer diameter of the container 130 such that when the cap 400 is placed on top of the container 130 the cylinder created has a substantially uniform circumference. While FIG. 4B provides a cap 400 having a circular top 402, in some embodiments, the top of the cap 400 may have an angular shape to facilitate handling, and in further embodiments, the top of the cap 400 may have a domed shape to increase the area inside the cap 400, to provide additional shielding, or for aesthetic appeal.

Figure 4C:
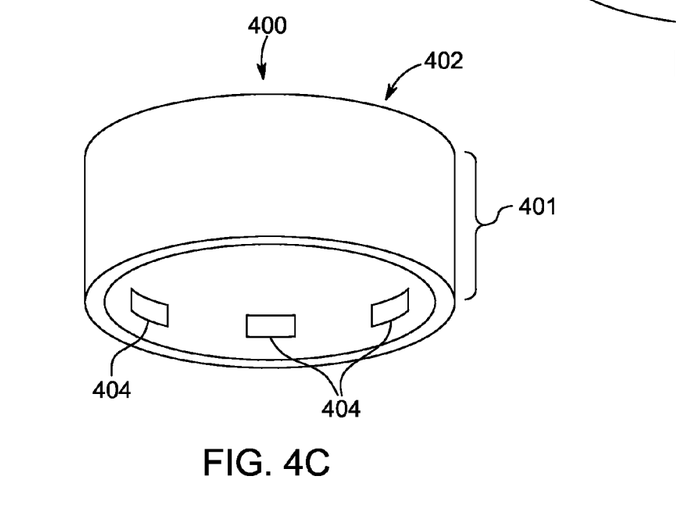

In various embodiments as illustrated in FIG. 4A, the cylindrical lower portion 401 of the cap 400 may include an interior, continuous or discontinuous groove 403 positioned to correspond with the upper portion of the outer surface of the collar 120, and the interior groove 403 may provide a means for attaching to the collar 120. For example, in some embodiments, in which a magnetic ring is provided in the upper portion of the outer surface of the collar, the interior groove 403 of the cap 400 may include a metallic ring positioned to interact with the magnetic ring in the upper portion of the outer surface of the collar. In other embodiments as illustrated in FIG. 4C, one or more magnets 404 may be provided on the inner surface of the lower portion 401 of the cap that are positioned to interact with a material in the upper portion of the outer surface of the collar, such as a magnetic material or a metallic material that is attracted to a magnet.

The cap 400 may be made from any material known in the art, and the choice of material may depend on the hazardous material held within the vial. In some embodiments, the cap 400 may be made from the same material as the container, and in other embodiments, the cap 400 may be made from a different material than the container. For example, in various embodiments, the cap 400 or portions thereof may be made from a polymeric material, metal, composite material, or combinations thereof, such as those described above. In some embodiments, the container 330 or portions thereof may be composed of a metal or metal alloy such as those described above. In particular embodiments, the container 330 may be designed to hold a radioactive material and may be composed of a material capable of blocking or reducing emission of high energy radioactive particles such as those described above.

According to various embodiments, the vial container with collar cap as described herein may allow ready disposal of disposable portions of the device. For example, in embodiments where the collar is made from inexpensive and disposable materials, the vial with collar may be readily disposed of, either at the source of the radiopharmaceutical, the site where the radiopharmaceutical test if performed, or some other approved disposal site. For example, the vial and collar assembly may be removed from the container and cap, such as, after any residual radiopharmaceutical present in the vial has decayed via radioactive decay to a safe level. At this point, the vial and collar assembly may be removed and disposed of in a suitable manner and the container and cap may be cleaned and reused. According to various embodiments, the cap 100 may further contain an inner liner, for example an adsorbent liner capable of adsorbing any radiopharmaceutical that may leak from the septum at the top of the vial. In other embodiments, the lower portion of the container 130 may contain an inner liner, such as an adsorbent liner to adsorb any radiopharmaceutical that may leak from the vial. These liners for the cap and/or container may be removable and disposable, after waiting sufficient time for any spilled radiopharmaceutical to decay to safe levels, and replaced with new liner material prior to insertion of a new vial.

Although various embodiments have been described in detail for the purpose of illustration, it is to be understood that such detail is solely for that purpose and that the disclosure is not limited to the disclosed embodiments, but, on the contrary, is intended to cover modifications and equivalent arrangements. For example, it is to be understood that this disclosure contemplates that, to the extent possible, one or more features of any embodiment can be combined with one or more features of any other embodiment.

What is claimed is:

1. A vial container comprising:
   a collar comprising an upper flange and a lower flange providing a vial groove on at least a portion of an inner surface of the collar, wherein a spring is disposed in the vial groove such that the spring is configured to hold at least part of a vial in the vial groove by pushing the vial toward the upper flange;
   a container configured to receive a lower portion of the collar within an interior of the container and to fixedly attach to the lower portion of the collar; and
   a cap configured to receive an upper portion of the collar within the cap and to removably attach to the upper portion of the collar.

2. The vial container of claim 1, wherein the collar comprises a first connector on the lower portion for facilitating an attachment with the container.

3. The vial container of claim 2, wherein the first connector is selected from the group consisting of a flex-ring, threads, a crimped portion, attachment pins, a metal portion, a magnetic portion, and combinations thereof.

4. The vial container of claim 2, wherein the collar comprises a second connector on the upper portion for facilitating an attachment with the cap.

5. The vial container of claim 4, wherein the second connector is selected from the group consisting of a flex-ring, threads, a crimped portion, attachment pins, a metal portion, a magnetic portion, and combinations thereof.

6. The vial container of claim 1, wherein the collar comprises one or more of a lower continuous or discontinuous groove on the lower portion, an upper continuous or discontinuous groove on the upper portion, and combinations thereof.

7. The vial container of claim 1, wherein the collar comprises a magnetic material disposed in one or more of a lower continuous or discontinuous groove, an upper continuous or discontinuous groove, or a combination thereof.

8. The vial container of claim 1, wherein the upper flange provides an upper opening on the collar.

9. The vial container of claim 1, wherein the container comprises an inner continuous or discontinuous groove.

10. The vial container of claim 9, wherein the container further comprises a flex ring disposed in the inner continuous or discontinuous groove.

11. The vial container of claim 9, wherein the inner continuous or discontinuous groove comprises a magnetic material.

12. The vial container of claim 1, wherein the cap comprises a cylindrical lower portion having an interior continuous or discontinuous groove.

13. The vial container of claim 12, wherein the cap further comprises a flex-ring or magnetic material disposed in the interior continuous or discontinuous groove.

14. The vial container of claim 1, wherein the collar, the container, or combinations thereof comprise a connector for attaching to a device.

15. The vial container of claim 1, wherein the collar, the container, or combinations thereof comprise a flex-ring, threads, attachment pins, a metal portion, a magnetic portion, or combinations thereof.

16. A vial container comprising:
    a cap configured to receive an upper portion of a collar;
    a container configured to receive a lower portion of the collar; and
    the collar comprising a first connector on the lower portion for facilitating an attachment with the container, a second connector on the upper portion for facilitating an attachment with the cap, and an upper flange and a lower flange providing a vial groove on at least a portion of an inner surface of the collar, wherein a spring is disposed in the vial groove such that the spring is configured to hold at least part of a vial in the vial groove by pushing the vial toward the upper flange.

17. A vial container comprising:
    a collar comprising an upper flange and a lower flange providing a vial groove on at least a portion of an inner surface of the collar, wherein a spring is disposed in the vial groove such that the spring is configured to hold at least part of a vial in the vial groove by pushing the vial toward the upper flange;
    a cap configured to receive an upper portion of the collar; and
    a container configured to receive a lower portion of the collar.

* * * * *

UNITED STATES PATENT AND TRADEMARK OFFICE
CERTIFICATE OF CORRECTION

PATENT NO. : 9,757,306 B2  
APPLICATION NO. : 14/775988  
DATED : September 12, 2017  
INVENTOR(S) : Fazi et al.

Page 1 of 1

It is certified that error appears in the above-identified patent and that said Letters Patent is hereby corrected as shown below:

On the Title Page

In Column 1, below Item (65), insert Item -- (63) Related U.S. Application Data Continuation-in-Part of application No. 13/802,669, filed on Mar. 13, 2013, now Pat. No. 9,327,886. --.

In the Specification

In Column 1, Lines 6-16, delete "This application claims the benefit of U.S. application Ser. No. 13/802,669, now U.S. Pat. No. 9,327,886, filed Mar. 13, 2013 and entitled "Vial Container with Collar Cap," and which is incorporated herein in its entirety. This application is a U.S. National Phase entry under 35 U.S.C. §371 of International Application No. PCT/US2014/022448, filed Mar. 10, 2014, which claims the benefit of U.S. application Ser. No. 13/802,669, filed Mar. 13, 2013 and entitled "Vial Container with Collar Cap," and which is incorporated herein in its entirety" and insert -- This application is a U.S. National Phase entry under 35 U.S.C. § 371 of International Application No. PCT/US2014/022448, filed Mar. 10, 2014, which is a continuation-in-part of U.S. application Ser. No. 13/802,669, now U.S. Pat. No. 9,327,886 filed Mar. 13, 2013 and entitled "Vial Container with Collar Cap," and which is incorporated herein in its entirety. --, therefor.

Signed and Sealed this  
Third Day of April, 2018

Andrei Iancu  
*Director of the United States Patent and Trademark Office*